US006656142B1

United States Patent
Lee

(12) 
(10) Patent No.: US 6,656,142 B1
(45) Date of Patent: Dec. 2, 2003

(54) SPLINT FOR MEDICAL TREATMENT

(76) Inventor: Young-Chan Lee, 828-4 Yangdeok-ri, Samseong-myun, Eumseong-gun, Chungcheongbuk-do (KR)

(*) Notice: Subject to any disclaimer, the term of this patent is extended or adjusted under 35 U.S.C. 154(b) by 0 days.

(21) Appl. No.: 10/319,224

(22) Filed: Dec. 13, 2002

(51) Int. Cl.$^7$ .................................................. A61F 5/00
(52) U.S. Cl. ............................... 602/5; 602/8; 128/881
(58) Field of Search ........................... 602/5–9, 20, 21, 602/23; 128/845, 846, 881

(56) References Cited

U.S. PATENT DOCUMENTS

| | | | | |
|---|---|---|---|---|
| 6,383,615 B2 | * | 5/2002 | Otten | 428/206 |
| 6,475,253 B2 | * | 11/2002 | Culler | 51/295 |
| 2001/0024715 A1 | * | 9/2001 | Otten | 428/315.9 |

* cited by examiner

Primary Examiner—Michael A. Brown
(74) Attorney, Agent, or Firm—Ladas & Parry

(57) ABSTRACT

The present invention relates to a splint used for a medical treatment, and in particular to a splint for a medical treatment which is capable of preventing an infection through, a wound by providing an antibacterial treatment to a surface contacting with thee wound based on a good ventilation operation using a non-woven fabric. The medical splint according to the present invention includes an anti-bacteria cover formed of a multiple-cover polypropylene non-woven fabric added with an anti-bacterial agent, a hardening cover which is formed of a polyester added with a moisture hardening agent and includes a plurality of ventilation holes, and an outer cover which is formed of a divided microfiber and includes an attaching means attached to the anti-bacterial cover at an edge portion, wherein said anti-bacterial cover, hardening cover, and outer cover are sequentially formed.

7 Claims, 6 Drawing Sheets

PRIOR ART

PRIOR ART

SPLINT FOR MEDICAL TREATMENT

BACKGROUND OF THE INVENTION

1. Field of the Invention

The present invention relates to a splint used for a medical treatment, and in particular to a splint for a medical treatment which is capable of preventing an infection through a wound by providing an antibacterial treatment to a surface contacting with a wound based on a good ventilation operation using a non-woven fabric.

2. Description of the Background Art

In the case that a bone is cracked or broken by a certain accident, or in the case that a bone is damaged, a medical splint is generally used. Namely, a splint is adapted to safely cover a wound such as a bone broken portion in part or in entire for bonding a broken or cracked bone or fixing a broken bone.

In a gyps method which is widely used, a bandage coated with a plaster material is adapted to cover a wound portion. In the above gyps method, when a plaster bandage is covered to a bone broken portion, it is possible to effectively warp the wound portion. However, when a plaster material is hardened, the plaster material is contracted, so that a certain gap is formed between the plaster material and the wound. When there is formed a gap therebetween, it is impossible to effectively support the wound, and the wound becomes movable. Therefore, it is impossible to implement a desired medical treatment. In addition, in the above method, since the wound is covered to a certain thickness, it takes a long time to fully cover the wound. Since the wound covered by the bandage is not well ventilated, a lot of sweat is generated in the summer season. In the case that the bone is broken, since a patient has a splint for about 8 weeks, if the above period is in the summer season, itch or other problems may occur.

In order to overcome the above problems, as shown in FIGS. 1 and 2, a splint is introduced. A glass fiber 1 having a hardening agent therein is provided in the interior of the, splint. An inner cover 2 is provided in an inner side of the glass fiber 1, namely, in a portion contacting with a bone broken portion of a patient. In addition, an outer cover 3 is provided in an outer side of the glass fiber 1.

In the case that an elbow or knee is covered using the above splint, a wrinkled portion 4 is unavoidable formed. Namely, the wrinkled portion 4 is naturally formed due to a thickness of the glass fiber 1. When a formation ability capable of stably covering the wound along a curved portion of the same is decreased, the splint may be upwardly moved from the wound portion, so that it is impossible to stably support the wound portion. Therefore, it is impossible to implement a desired therapy with respect to the bone broken portion. In addition, the material of the splint is formed of a glass fiber, it is impossible to burn up the same for thereby causing an environmental problem. In addition, a respiratory organ disease and skin itch problem may occur due to the dusts of the glass fiber. Furthermore, in the conventional medical splint, it is impossible to implement a desired ventilation.

The inner cover which is closely contacted with the wound has various bacteria, so that the above bacteria may infect the wound. Therefore, it takes a long time to implement a desired therapy. In addition, various diseases may occur.

SUMMARY OF THE INVENTION

Accordingly, it is an object of the present invention to provide a splint for a medical treatment which overcomes the problems encountered in the conventional art.

It is another object of the present invention to provide a splint for a medical treatment which is capable of obtaining a good formation and ventilation, closely supporting a wound and preventing an infection of various bacteria.

To achieve the above objects, there is provided a splint for a medical treatment which includes an anti-bacteria cover formed of a multiple-cover polypropylene non-woven fabric added with an anti-bacterial agent, a hardening cover which is formed of a polyester added with a moisture hardening agent and includes a plurality of ventilation holes, and an outer cover which is formed of a divided microfiber and includes an attaching means attached to the anti-bacterial cover at an edge portion, wherein said anti-bacterial cover, hardening cover, and outer cover are sequentially formed.

BRIEF DESCRIPTION OF THE DRAWINGS

The present invention will become better understood with reference to the accompanying drawings which are given only by way of illustration and thus are not limitative of the present invention, wherein.

DETAILED DESCRIPTION OF THE PREFERRED EMBODIMENTS

Figure 1:
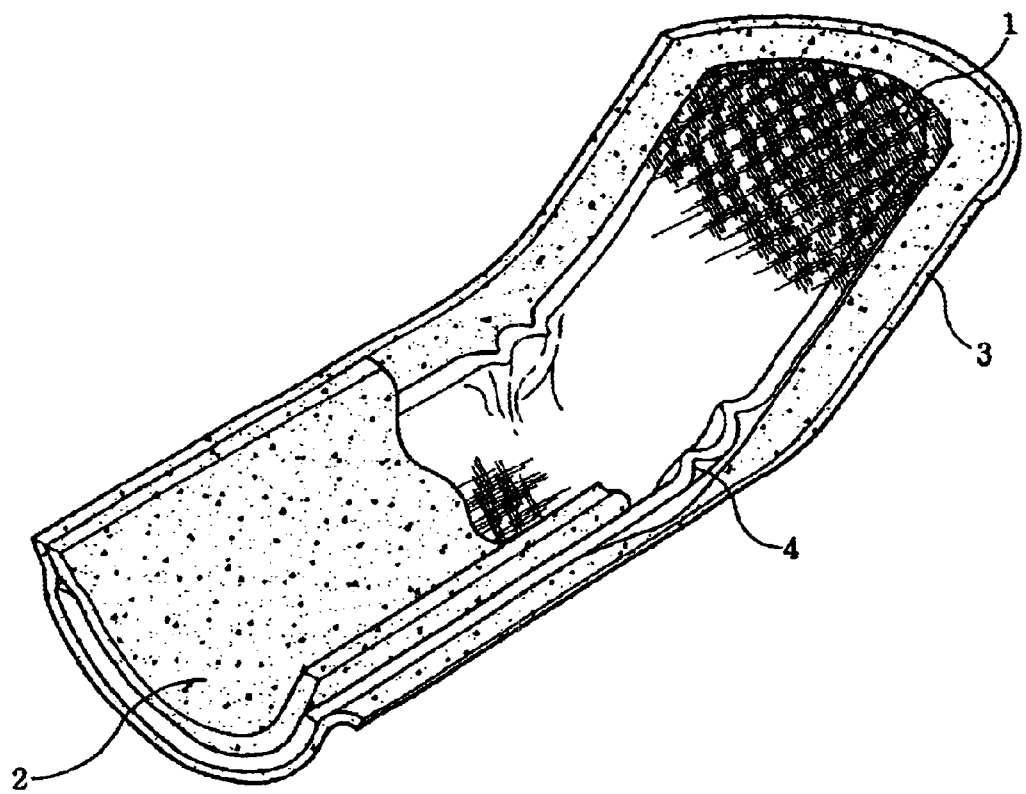
FIG. 1 is a perspective view illustrating a part of a conventional splint for a medical treatment.
Figure 2:
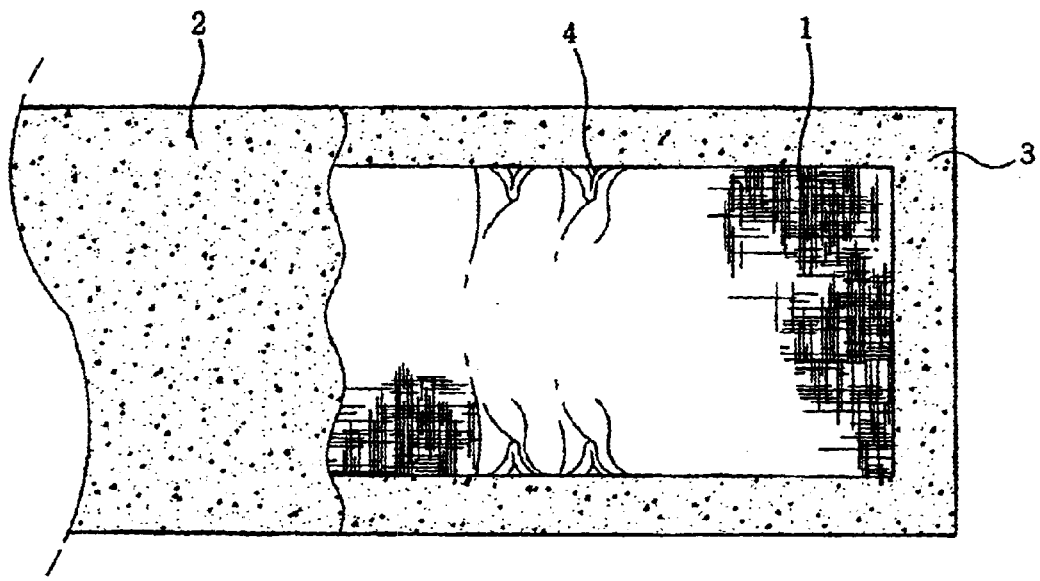
FIG. 2 is a plan view of FIG. 1.
Figure 3:
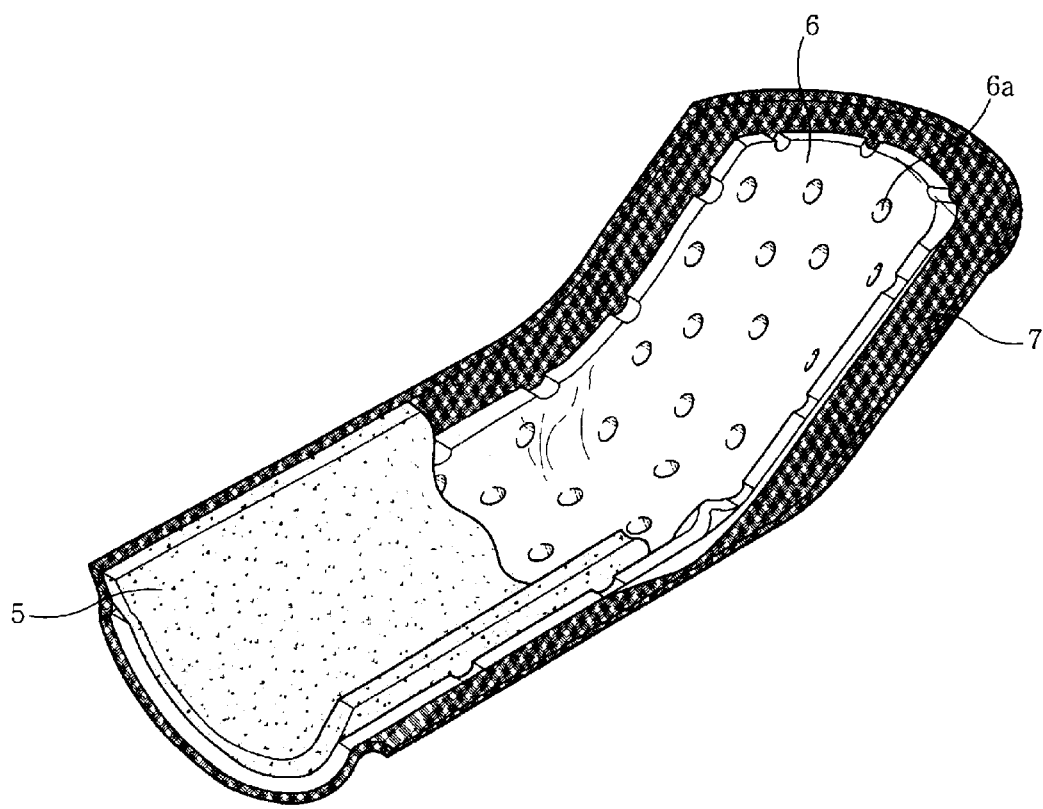
FIG. 3 is a perspective view illustrating a medical splint according to an embodiment of the present invention.
Figure 4:
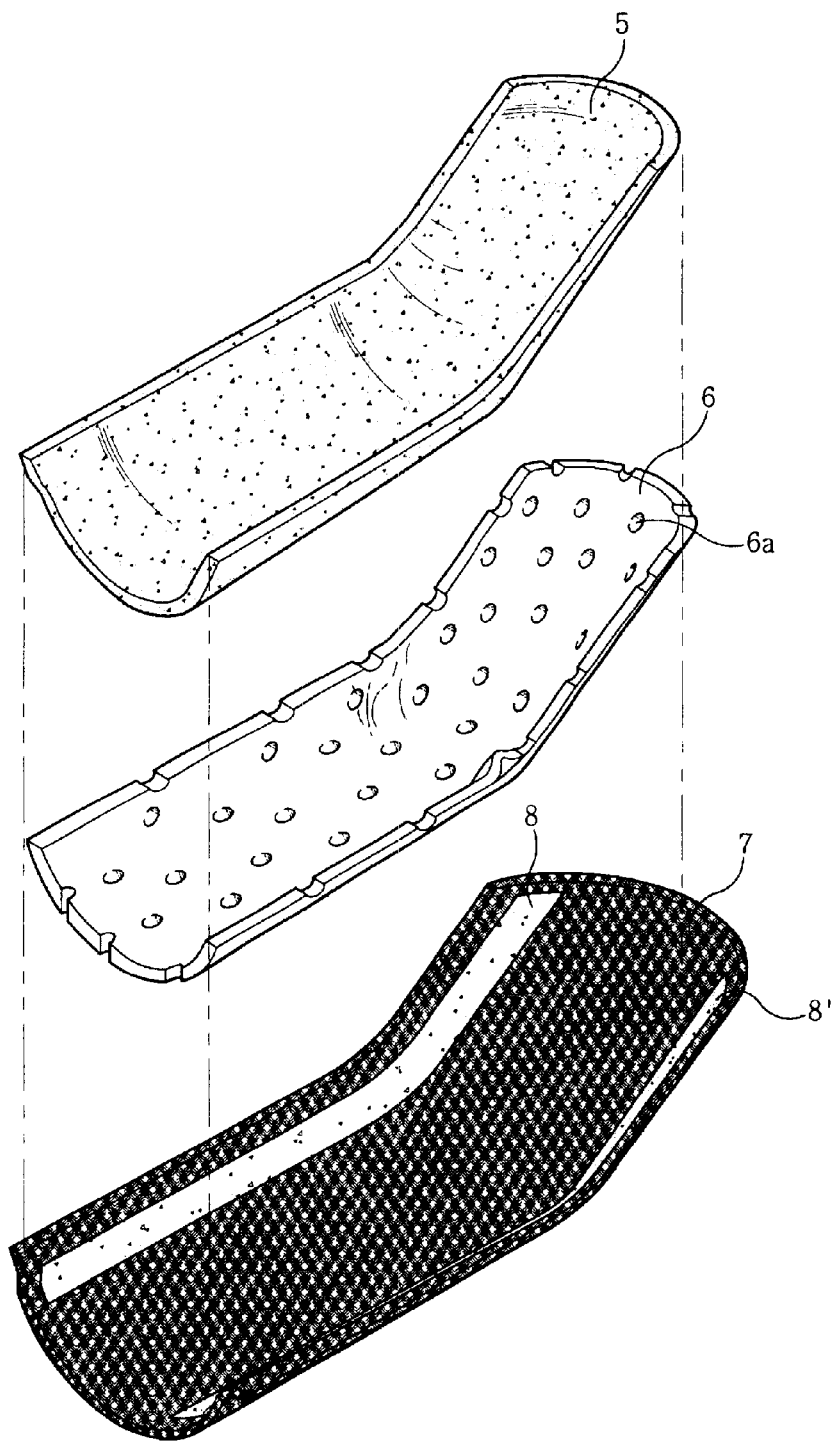
FIG. 4 is a disassembled perspective view illustrating a medical splint according to an embodiment of the present invention.
Figure 5:
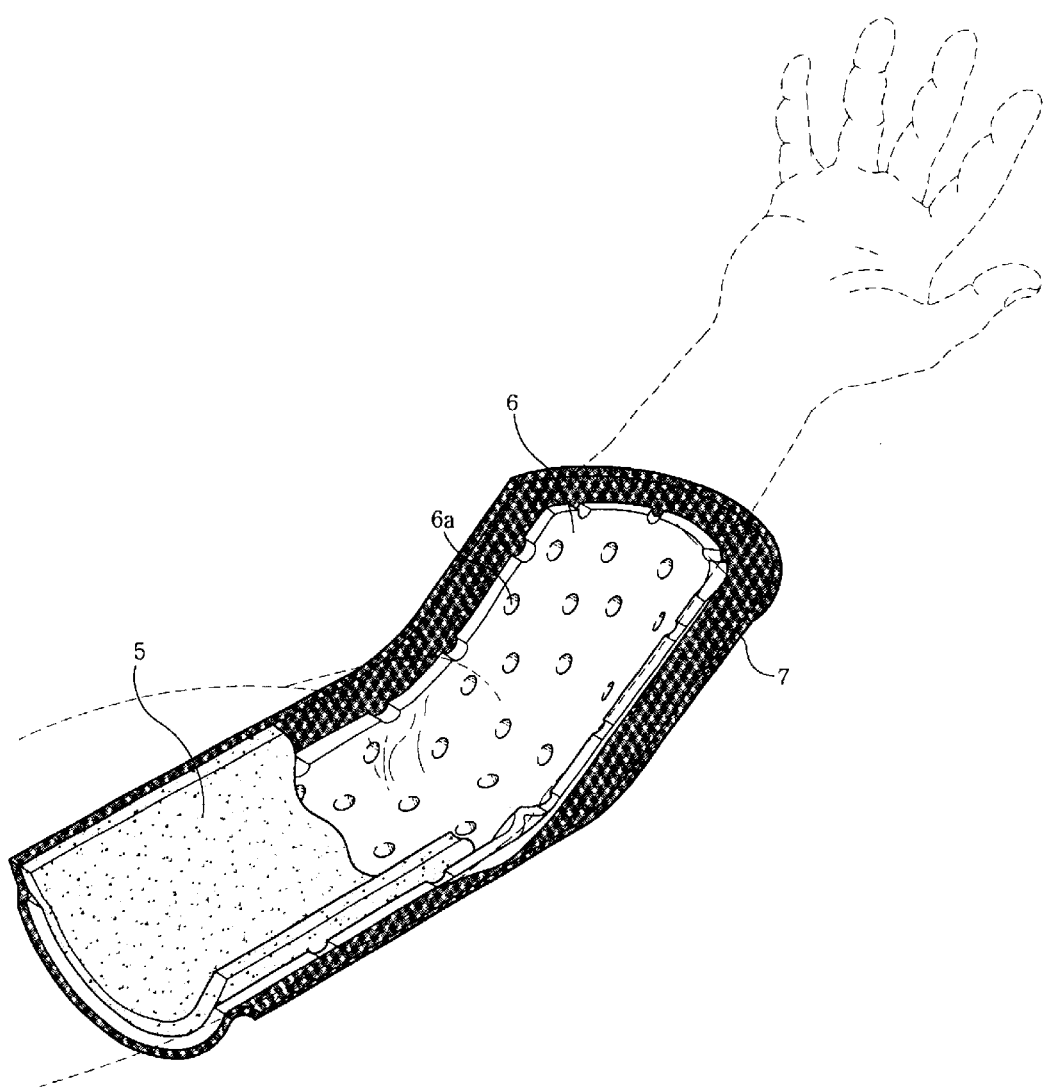
FIG. 5 is a view illustrating a state of use of a medical splint according to an embodiment of the present invention.

FIG. 3 is a perspective view illustrating a medical splint according to an embodiment of the present invention, FIG. 4 is a disassembled perspective view illustrating a medical splint according to an embodiment of the present invention, and FIG. 5 is a view illustrating a state of use of a medical splint according to an embodiment of the present invention.

As shown therein, a medical splint according to an embodiment of the present invention includes an antibacterial cover 5 which is formed of a plurality of non-woven fabrics manufactured using a polypropylene and includes an antibacterial agent and covers a wound, a hardening cover 6 which is formed of a polyester and includes a water hardening agent which is capable of hardening water and a ventilation hole 6a, and an outer cover 7 which is attached to an edge portion of the antibacterial cover by attaching members 8, 8' and covers the hardening cover 6, for thereby supporting the wound.

The medical splint according to an embodiment of the present invention absorbs moisture by soaking the same in water and is attached to a wound before the medical splint is hardened by the moisture hardening agent in a state that the medical splint has moisture and is fixed by a bandage. Here, as a moisture hardening agent, a polyurethane resin is preferably used.

At this time, the antibacterial cover 5 is formed of a plurality of non-woven fabrics, so that water fast flows to the hardening cover 6 through the antibacterial cover 5, whereby a plurality of non-woven fabrics absorb a lot of water. After the moisture hardening agent absorbs water, a plurality of non-woven fabrics are well ventilated. In addition, the antibacterial agent added to the antibacterial cover 5 prevents a growth of harmful bacteria. After the hardening cover 6 is hardened, the water does not penetrate for thereby preventing bad smell and band feeling. The antibacterial agent added to the antibacterial cover 5 is formed of arbekacin or zinc omadine. In another embodiment of the present invention, another anti-bacterial agent which may be directly used to skin, may be used.

The ventilation hole 6a is formed in the hardening cover 6. Therefore, after the hardening agent is closely attached to the wound, the hardening cover 6 is fast hardened, so that a wrinkled portion is not formed even in a curved portion like an elbow, knee compared to the conventional medical splint.

Here, the outer cover 7 is formed of a divided microfiber. Preferably, the outer cover 7 is formed of a divided microfiber formed of a polyamide and polyester. Attaching members 8, 8' are formed in an edge portion of the outer cover 7 for thereby integrally fixing the anti-bacterial cover 5, the hardening cover 6, and the outer cover 7 based on an attachment to an edge portion of the anti-bacterial cover 5. The above attaching members 8, 8' are preferably formed of a double-side bond tape.

Figure 6:
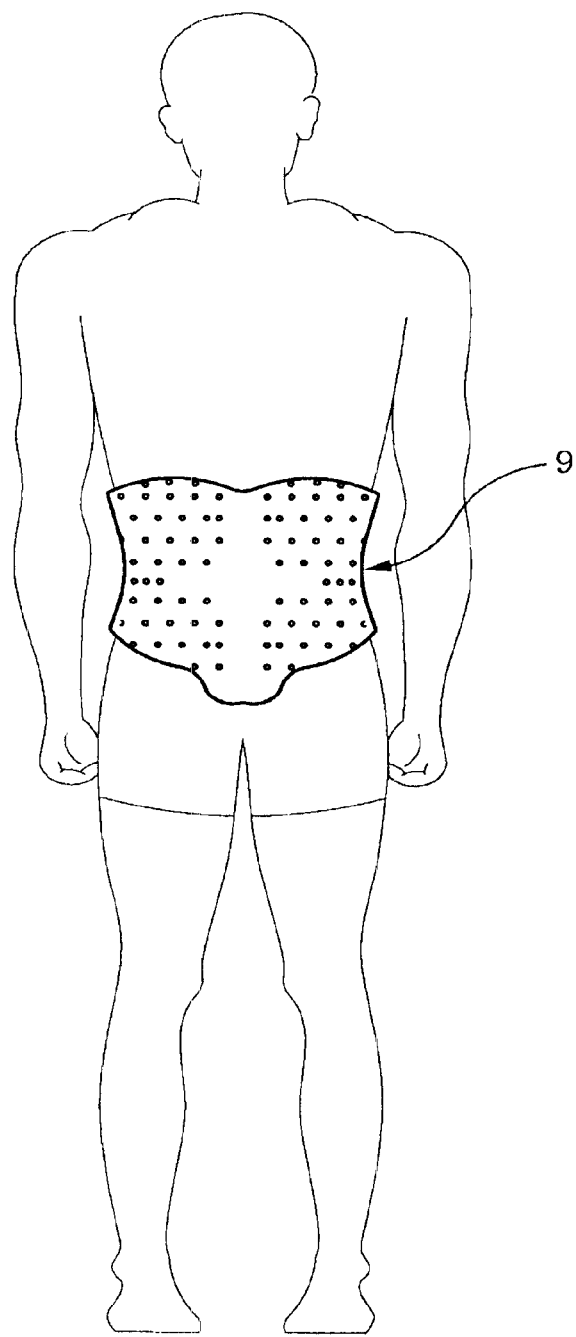
FIG. 6 is a view illustrating a state of use of a medical splint according to another embodiment of the present invention.

FIG. 6 is a view illustrating a medical splint according to another embodiment of the present invention.

As shown therein, a medical splint in which the anti-bacterial cover 5, the hardening cover 6 and the outer cover 7 are sequentially formed is used to a waist broken portion 9.

The anti-bacterial effect of the anti-bacterial cover was tested by FITI testing and research institute which is an organ authorized by the government.

EXAMPLE 1

Experiment Method

As seen in Table 1, $1.6 \times 10^5$ number of staphylococcus aureus ATCC 6538 were added to al polypropylene non-woven fabric and a polypropylene non-woven fabric having Arbekacin as an anti-bacterial agent, respectively, and 18 hours were passed. Thereafter, the number of remaining bacteria was computed. In the same manner, $1.4 \times 10^5$ number of another bacteria of Klebsiella pneunoniae ATCC 4352 were added, and the anti-bacterial test was repeatedly performed.

Result of Experiments

After 18 hours were passed when the bacteria were inputted, as a result of the first experiment, the number of bacteria were increased to $6.6 \times 10^5$ in the polypropylene non-woven fabric, and in the polypropylene non-woven fabric having Arbekacin, the number of bacteria was sharply decreased to below 10. As a result of the second experiment, in the polypropylene non-woven fabric, the number of the bacteria was increased to $5.2 \times 10^5$, and in the polypropylene non-woven fabric having Arbekacin, the number of the bacteria was decreased below 10.

The above results of the experiments were shown in Table 1.

TABLE 1

| | | Polypropylene non-woven fabric | Polypropylene non-woven fabric having anti-bacteria agent |
|---|---|---|---|
| Staphylococcus aureus ATCC 6538 | Initial stage | $1.6 \times 10^5$ | $1.6 \times 10^5$ |
| | After 16 hours | $6.6 \times 10^6$ | Below 10 |
| | Decrease ratio (bacteriostatic ratio) | | 99.9% |
| Klebsiella pneunoniae ATCC 4352 | Initial stage | $1.4 * 10^5$ | $1.4 \times 10^5$ |
| | After 16 hours | $5.2 \times 10^6$ | Below 10 |
| | Decrease ratio (bacteriostatic ratio) | | 99.9% |

As described above, the medical splint according to the present invention is capable of preventing an infection by harmful bacteria and itch in such a manner that a non-woven fabric having an anti-bacterial agent directly contacts with a human skin. In addition, the hardening cover includes a ventilation hole, and the outer cover is formed of a divided microfiber, so that a penetration is improved after the splint is hardened for thereby implementing a pleasantness state.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. A medical splint, comprising:
    an anti-bacteria cover formed of a multiple-cover polypropylene non-woven fabric added with an anti-bacterial agent;
    a hardening cover which is formed of a polyester added with a moisture hardening agent and includes a plurality of ventilation holes; and
    an outer cover which is formed of a divided microfiber and includes an attaching means attached to the anti-bacterial cover at an edge portion, wherein said anti-bacterial cover, hardening cover, and outer cover are sequentially formed.

2. The splint of claim 1, wherein said anti-bacterial agent is arbekacin or zinc omadine.

3. The splint of claim 1, wherein said moisture hardening agent is a polyurethane resin.

4. The splint of claim 1, wherein said divided microfiber is formed of polyamide and polyester.

5. The splint of claim 4, wherein said moisture hardening agent is a polyurethane resin.

6. The splint of claim 4, wherein said attaching means is a double-side bond tape.

7. The splint of claim 1, wherein said attaching means is a double-side bond tape.

* * * * *